United States Patent
Gleichauf et al.

(10) Patent No.: US 7,172,740 B2
(45) Date of Patent: *Feb. 6, 2007

(54) STERILE CONTAINER

(75) Inventors: Wilhelm Gleichauf, Tuttlingen-Moehringen (DE); Mariana Jakab, Tuttlingen (DE); Friedrich-Wilhelm Oertmann, Tuttlingen (DE); Torsten Renner, Eisenberg (DE); Stefan Schuster, Tuttlingen (DE); Wolfgang Schwanke, Rietheim-Weilheim (DE)

(73) Assignee: Aesculap AG & Co. KG, Tuttlingen (DE)

( * ) Notice: Subject to any disclaimer, the term of this patent is extended or adjusted under 35 U.S.C. 154(b) by 194 days.

This patent is subject to a terminal disclaimer.

(21) Appl. No.: 10/845,780

(22) Filed: May 13, 2004

(65) Prior Publication Data

US 2004/0256269 A1 Dec. 23, 2004

Related U.S. Application Data

(63) Continuation of application No. PCT/EP02/09749, filed on Aug. 31, 2002.

(30) Foreign Application Priority Data

Nov. 15, 2001 (DE) ................ 101 56 935

(51) Int. Cl.
 *A61L 9/00* (2006.01)
(52) U.S. Cl. .............. 422/300; 141/66; 141/325; 141/326; 206/439; 220/371; 422/292; 422/297
(58) Field of Classification Search ........... 422/292, 422/294, 295, 296, 310, 300, 297; 206/439, 206/484.1, 363, 370; 220/371; 141/57, 141/286; 53/84, 97
See application file for complete search history.

(56) References Cited

U.S. PATENT DOCUMENTS

| 4,372,921 | A | * | 2/1983 | Sanderson et al. ......... 422/300 |
| 4,512,498 | A | | 4/1985 | Leibinger |
| 4,551,311 | A | * | 11/1985 | Lorenz ...................... 422/300 |
| 4,661,326 | A | | 4/1987 | Schainholz |
| 4,783,321 | A | * | 11/1988 | Spence ....................... 422/300 |
| 5,176,884 | A | * | 1/1993 | Taschner et al. ............ 422/292 |
| 5,346,075 | A | | 9/1994 | Nichols et al. |
| 5,524,755 | A | * | 6/1996 | Deeds ........................ 206/370 |
| 5,690,713 | A | * | 11/1997 | Bowerman et al. .......... 55/490 |
| 6,053,914 | A | * | 4/2000 | Eggers et al. ................ 606/48 |
| 6,077,485 | A | * | 6/2000 | Baker ........................ 422/300 |
| 6,145,687 | A | | 11/2000 | Nichols et al. |

FOREIGN PATENT DOCUMENTS

| DE | 82 13 351 | 10/1982 |
| DE | 35 00 026 | 7/1986 |

* cited by examiner

Primary Examiner—Krisanne Jastrzab
(74) Attorney, Agent, or Firm—Lipsitz & McAllister, LLC

(57) ABSTRACT

The invention relates to a sterile container, in particular for the receipt and sterile storage of surgical instruments or material, comprising a receiving chamber and a gas exchange opening that can be sealed using a sterile filter. The aim of the invention is to prevent undesired liquid from reaching the sterile filter. To achieve this, the exterior of the lid is provided with at least one inflow edge, which faces away from the gas exchange opening, and falls away towards the exterior in relation to a lid plane.

45 Claims, 9 Drawing Sheets

STERILE CONTAINER

This application is a continuation of international application number PCT/EP02/09749 filed on Aug. 31, 2002.

This application claims the benefit of German Patent Application No. 101 56 935.1 filed Nov. 15, 2001.

BACKGROUND OF THE INVENTION

The invention relates to a sterile container, in particular for the holding and sterile storage of surgical instruments or material, comprising a holding space, which is defined by a container base and container walls, a lid for closing the holding space and a gas exchange opening, which can be closed off by a sterile filter.

Sterile containers of the type described in the introduction, once they have been filled, for example with surgical instruments and/or material, are sterilized in a sterilizer using steam or other media. Consequently, the problem frequently arises whereby the lid, after the sterilizing operation, is wetted with liquid, in particular with residual condensate. This can then reach the sterile filter in an undesired manner. The same problem arises if the sterile container is inadvertently exposed to any liquid.

Therefore, it is an object of the present invention to improve a sterile container of the type described in the introduction in such a manner that it is impossible for any liquid to reach the sterile filter in an undesired manner.

SUMMARY OF THE INVENTION

According to the invention, this object is achieved by virtue of the fact that on the outer side of the lid there is provided at least one inflow edge which faces away from the gas exchange opening and slopes downward toward the outside relative to a lid plane.

This configuration allows gas or steam to flow along the inflow edge to the gas exchange opening and through the latter into the holding space, or vice versa. By contrast, a liquid which reaches the lid can flow off away from the gas exchange opening. This prevents water from accumulating on the lid, and consequently there is no risk of liquid being able to flow onto the sterile filter.

To ensure that the liquid can flow off reliably and under all conditions, it is advantageous if an angle of inclination which is included by the inflow edge and the lid plane is at least 1°.

There is advantageously provided a protective element which covers the sterile filter at a spacing therefrom. This protects the sterile filter from mechanical loads and from being acted on by liquid; a protective element which curves convexly away from the lid has proven advantageous with a view to avoiding accumulations of liquid on the protective element.

To make it easier for liquid which is present on the protective element to flow away, it is expedient if the protective element is disposed on an outer side of the sterile container.

According to a preferred embodiment of the invention, it is possible to provide that the lid, on its outer side, has a seating surface for seating the protective element, which surrounds the gas exchange opening. This allows the protective element to be attached or connected to the lid in a defined way. Furthermore, it advantageously fits into the lid, for example in order to form a common surface.

To ensure as flat an overall shape as possible, it is advantageous if the seating surface comprises an annular surface which runs parallel to the lid plane and is set back in the direction of the holding space.

To ensure that it is impossible for any liquid to reach the sterile filter in an undesired way, it is advantageous if the protective element completely covers the gas exchange opening and the seating surface. Liquid which is present on the protective element can then flow off the protective element without reaching the seating surface surrounding the gas exchange opening or the sterile filter covering the gas exchange opening.

It is preferably possible for there to be provided support surfaces for the purpose of supporting the protective element connected to the lid. The protective element is supported on the lid via these support surfaces.

To ensure that a defined spacing can be maintained between the protective element and the lid, it is preferable for the protective element to comprise spacer elements.

It is expedient if the protective element comprises a reinforcing frame. In particular in the case of protective elements made from soft or elastic materials, or also in the event of exposure to hot steam, the protective element is stabilized in its desired shape by the reinforcing frame.

It is particularly advantageous if the reinforcing frame comprises webs which cross one another and run substantially parallel to the lid surface. A reinforcing frame of this type can be produced particularly easily and offers sufficient stability while consuming only minimal material.

To keep the structural outlay and number of components of the sterile container small, it is expedient if the spacing elements are formed by projections and/or at least in part by the webs. Therefore, the projections and/or webs fulfil a dual function. Firstly, they reinforce the protective element, and secondly they ensure a desired spacing between the protective element and the lid.

To facilitate assembly of the sterile container and to increase the ease of maintenance, in a preferred embodiment of the invention there is provided at least one snap-action connection for connecting the protective element to the lid.

A further advantage ensues if the at least one snap-action connection is provided for connection of the protective element to a rim, which includes latching recesses, of the gas exchange opening. In particular in the case of protective elements which are not of rotationally symmetrical configuration, it is in this way possible to achieve a defined positioning of the protective element on the lid. The snap-action connection makes it easy to connect the protective element to the lid and release it again from the latter.

A particularly compact overall shape of the sterile container results if the at least one snap-action connection comprises elastic spring arms which project away from the protective element toward the lid and are provided with a latching projection. Moreover, it is in this way easy for the protective elements to be clipped to the lid, for example to the rim of the gas exchange opening.

The protective element itself could be provided with openings in order to allow gas exchange with the filter unit through the protective element to the gas exchange opening. However, it is particularly advantageous if there is provided, between the protective element and the lid, at least one opening for the passage of gas, which is in fluid communication with the gas exchange opening. This means that there is no need for any additional perforation in the protective element. The opening for the passage of gas is formed solely by the corresponding shape of the protective element and of the lid. Liquid which is present on the protective element can completely flow off the protective element without further covering of apertures in the protective element.

To additionally suppress penetration of liquid onto the sterile filter, it is advantageous if the opening for the passage of gas is arranged in such a way that it becomes possible for gas to flow in a direction of flow running substantially transversely with respect to the flow-permitting direction through the sterile filter.

A particularly flat overall shape results if the opening for the passage of gas, in cross section, has a double-convex lens shape. Furthermore, a run-off channel for liquids is formed by the lid surface, which is curved concavely in order to form the double-convex lens shape.

To allow gas exchange through the gas exchange opening with stacked sterile containers, it is expedient if the lid has at least one spacer element for stacking a further sterile container on the sterile container.

It is preferable for the inflow edge to be disposed between two spacer elements. This allows sufficient inclination of the inflow edge to enable liquid which has reached the lid to flow off.

To enable a plurality of sterile containers to be stacked safely on top of one another, it is expedient if the spacer elements comprise at least three projections facing away from the outer side of the sterile container.

In an advantageous embodiment of the invention, it is possible to provide that the seating surface is delimited by the at least one inflow edge and the at least one spacer element. This enables liquid to flow from the spacer element onto the inflow edge and then to be directly discharged from the latter.

To enable the protective element to be fitted into the lid surface without free edges being visible in the transition between the protective element and the lid, it is expedient if the spacer elements comprise or adjoin the support surfaces.

The sterile container can be produced particularly easily and inexpensively if the lid, the at least one spacer element, the seating surface and the at least one inflow edge are formed integrally.

To further simplify construction of the sterile container, it is advantageous if there is provided a filter unit, which comprises the sterile filter, a carrier and a holding element, and if the sterile filter is held between the carrier and the holding element.

The filter unit can be exchanged particularly easily, thereby increasing ease of maintenance of the sterile container, if the filter unit is in single-piece form, and if the carrier, the sterile filter and the holding element are nonreleasably connected, in particular by welding or adhesive bonding, to one another.

In a further preferred embodiment of the invention, it is possible to provide that the filter unit is mounted moveably, that the filter unit, in a closed position, closes a flow path and, in a flow-permitting position, opens the flow path, so that gas exchange in the closed position is possible only through the sterile filter and in the flow-permitting position is possible through the sterile filter and/or through the flow path. This means that the filter unit can be transferred into the closed position or the flow-permitting position on demand, depending on the level of gas and/or steam throughput which is desired.

To avoid damage to the sterile container and to simplify its overall structure, it is advantageous if there is provided a pressure-relief valve, if the pressure-relief valve is disposed in such a way that in a basic position it adopts a closed position, if it adopts a flow-permitting position when a pressure in a vicinity of the sterile container exceeds a pressure in the sterile container by a predetermined pressure difference, and if the pressure-relief valve forms the filter unit. The filter unit therefore serves firstly as a filter and secondly as a pressure-relief valve. Therefore, separate provision of a pressure-relief valve is no longer required.

To increase the stability of the lid, which is advantageous in particular in the case of large gas exchange openings, the gas exchange opening comprises at least one stiffening element for stiffening the lid. This can be achieved, for example, by webs or carriers which span the gas exchange opening.

It is preferable for the at least one stiffening element to be formed by a web spans the gas exchange opening. This web simultaneously serves as additional protection for the sterile filter.

In principle, the stiffening element could adjoin the seating surface, which runs parallel to the lid plane and is set back toward the holding space, and could therefore likewise be set back toward the holding space. However, it is expedient if the at least one stiffening element is offset in a direction away from the holding space relative to the outer side of the lid. This enables the condensed fluid which forms on the stiffening element to flow away from the stiffening element without reaching the sterile filter through the gas exchange opening.

To provide the sterile filter with even better protection against the penetration of fluids, in a preferred embodiment of the invention it is provided that there is a fluid-retaining element for preventing fluid from flowing in from the outer side of the lid through the gas exchange opening. This prevents any form of fluids, in particular including condensate, from being able to reach the sterile filter.

In principle, the fluid-retaining element could be disposed on an inner side of the lid. However, it is advantageous if the fluid-retaining element is disposed on the outer side of the lid and surrounds the gas exchange opening at least in sections. This right from the outset prevents fluids from being able to reach the region of the gas exchange opening.

In principle, the fluid-retaining element could also be formed by a membrane which spans the gas exchange opening. However, better gas exchange can be achieved if, in a preferred embodiment of the invention, the fluid-retaining element is formed as a rim which protrudes from the outer side of the lid. Moreover, a rim of this type can be produced particularly easily and inexpensively.

To keep fluids as far away from the gas exchange opening as possible, it is expedient if the fluid-retaining element is disposed at a spacing from the gas exchange opening. Furthermore, the region which adjoins the gas exchange opening and is protected from the penetration of fluids can serve, for example, as a seating surface.

It is preferable for the protective element to completely cover the gas exchange opening and the fluid-retaining element. Consequently, fluids which flow off the protective element must first overcome the fluid-retaining element before they are able to reach the sterile filter through the gas exchange opening.

The sterile container can be produced particularly easily and favorably if the lid is made from a plastic, in particular from polyether ether ketone (PEEK) or polyphenyl sulfone (PPSU).

BRIEF DESCRIPTION OF THE DRAWINGS

The following description of a preferred embodiment of the invention, in conjunction with the drawing, serves to provide a more detailed explanation. In the drawing.

DETAILED DESCRIPTION OF THE INVENTION

Figure 1:
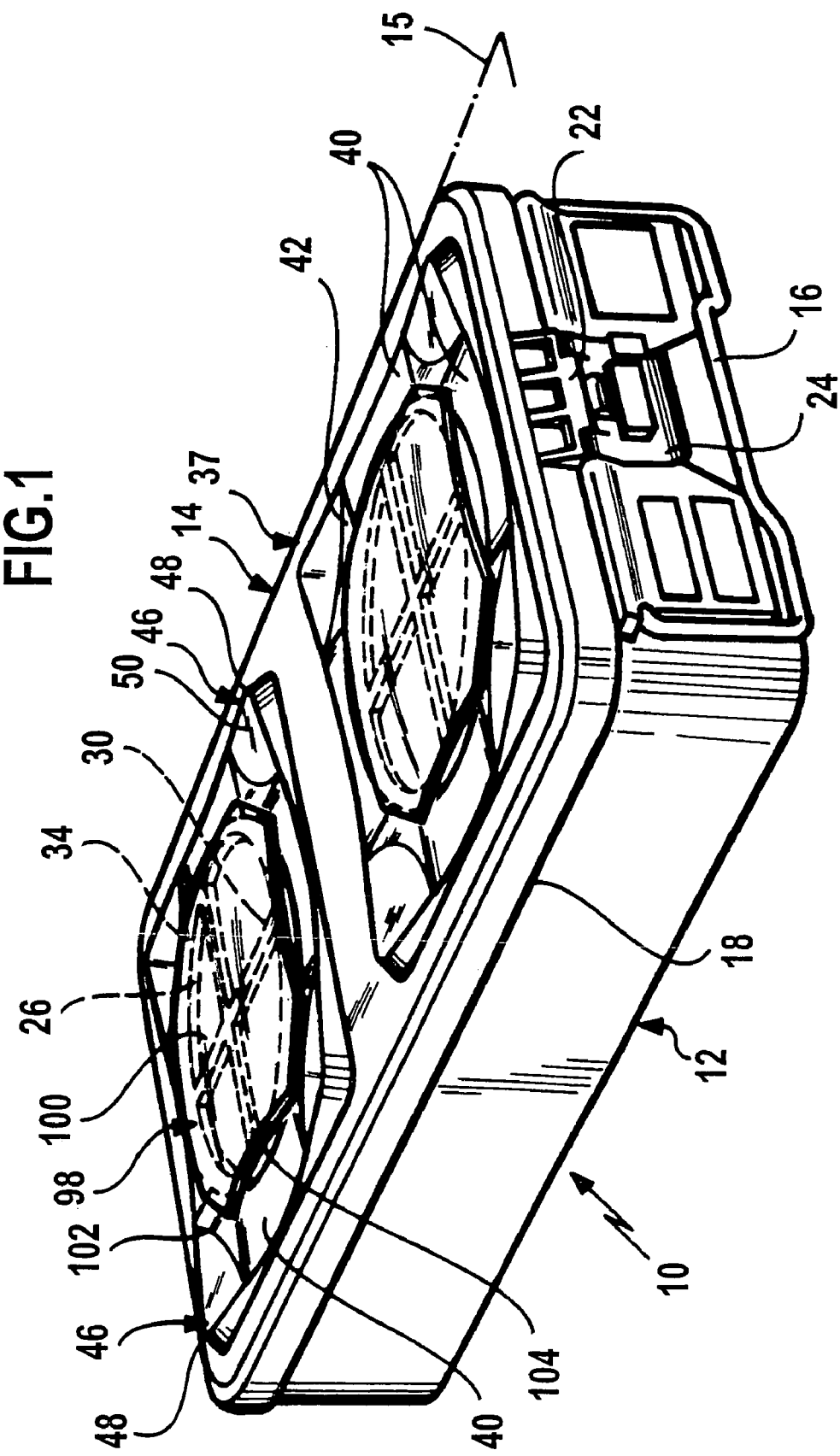
FIG. 1 shows a perspective overall view of a sterile container.

FIG. 1 illustrates a sterile container, which is denoted overall by reference numeral 10 and comprises a substantially tub-like, cuboidal container 12 for holding, for example, surgical instruments or material, and a lid 14. Pivotably mounted carry handles 16 are disposed at the end faces of the container 12.

The structure of the lid 14 is explained in more detail with reference to FIGS. 2 to 9.

The lid 14 is provided with an encircling rim 18 which projects perpendicularly from a lid plane 15, so that the lid 14 completely covers and partially engages around the container 12. A sealing rim 20, between which and the rim 18 a seal (not shown) can be inserted, runs parallel to and at a spacing from the rim 18. When the lid 14 has been fitted, the sealing rim 20 is located inside the container 12. The seal makes it possible to produce a gastight connection between the lid 14 and the container 12.

At its narrow end sides, the lid 14 in each case has a bearing bracket 22, on which a resilient closure flap 24 can pivot about a pivot axis running parallel to a pivot axis of the carry handle 16 when the lid 14 is seated on the container 12.

The lid 14 has two symmetrically disposed circular openings 26, which have an opening rim 28 which faces parallel to the lid plane 15 and on which four webs 30, which run perpendicularly toward one another and meet in the center of the opening 26, for stiffening the lid, are disposed symmetrically. Between each pair of webs 30 disposed at the opening rim 28, two indentations 32 and 33 are cut symmetrically into the opening rim 28.

The opening 26 is surrounded by an annular surface 34, which runs parallel to the lid plane 15 but is set back toward an underside 36 of the lid. As a result, an inner annular edge 38 is formed on a top side 37 of the lid and an outer annular edge 39 is formed on the underside 36 of the lid. The annular edge 38 is adjoined by four inflow edges 40 and four support surfaces 42 which alternate with one another. The inflow edges 40 are curved concavely away from the lid top side 37 and are inclined outward, so that an inclined plane with an angle of inclination 44 between the inflow edge 40 and the lid plane 15 of approximately 2° is formed.

The support surfaces 42 run parallel to the lid plane 15 and, when seen in plan view, are approximately in the shape of a trapezoid, but in each case with concavely curved base edges. The longer of the two base lines of the support surface 42 is adjoined by a three-sided pyramid 46, which has a base area which is substantially in the shape of an isosceles right-angled triangle. An apex 48 of the pyramid lies just above the base sides, which intersect at right angles, of the base surface, slightly offset toward the opening 26.

This results in the formation of a run-off surface 50 which is approximately in the shape of an isosceles, right-angled triangle which is inclined toward the support surface 42. The support surface 42 is offset away from the lid top side 37, parallel to the lid plane 15.

The overall result, therefore, is an approximately square structure on the lid 14, which is formed by four pyramids 46, which are each seated in the corners of the square, the side faces of the square running parallel to sides of the lid 14. The inflow edges 40 are therefore inclined perpendicularly toward the sides of the lid 14. The structure has a total of two planes of symmetry running parallel to the sides of the lid 14. On its side facing away from the opening 26, the inflow edge 40 extends down to the level of the lid plane 15. When the lid is seen from the side, therefore, the result is approximately a concave shape, facing away from the lid top side 37, from the apex 48 of the pyramid 46 in a corner of the square structure to the apex 48 of the pyramid 46 in an adjacent corner of the structure.

Adjacent to the indentations 32 and 33 are disposed a total of four hollow-cylindrical, open sleeves 52 protruding from the underside 36 of the lid. A filter cartridge 54 is mounted resiliently on these sleeves. The filter cartridge comprises an approximately octagonal filter holder 58, which is provided with a carrier rim 56 and has an annular filter receiver 60 for accommodating a circular long-term filter 62. An annular recess 64, which is configured with a larger diameter than the filter receiver 60, is used to accommodate a holding ring 66, which in cross-section has an L-shaped profile, one limb of which presses the long-term filter 62 into the filter receiver 60 and the other limb of which engages against the recess 64. The holding ring 66 is provided with an annular ring groove, which in cross-section includes slightly more than half of a circle, for accommodating a sealing ring 70.

Four mounting sleeves 74, corresponding to the sleeves 52 disposed on the lid 14, protrude from a filter holder base 72 toward the lid; these mounting sleeves are open from the filter holder base 72, and their other, closed end face 76 is provided with a central through opening 78 whose diameter corresponds to that of the sleeve 52. To mount the filter cartridge 54, the four mounting sleeves 74 are pushed over the sleeves 52, a coil spring 80 is in each case fitted over the sleeves 52, and then the mounting sleeves 74 of the filter holder base 72 are closed off with a stopper 82 which has a disk-like head 84 whose external diameter is matched to the internal diameter of the mounting sleeves 74. On account of the fact that the coil spring 80 is supported against the head 84 of the stopper 82, it presses the end face 76 onto the underside 36 of the lid.

The filter holder base 72 is provided with a total of twenty strip-like slots 86 of different lengths, with in each case five slots running parallel to one another and approximately covering the area of a quarter-circle. Slots 86 belonging to adjacent quarter-circles are in each case positioned perpendicular to one another. A protective web 88 is formed between each pair of slots 86. A strip 90, which faces away from the filter holder base 72 and from which, once again running parallel to the filter holder base 72, there protrudes a support web 92 facing away from the associated protective web 88 and in each case completely covering a slot 86, is disposed on each protective web 88. All the support webs 92 define a common plane on which the long-term filter 62 rests. Overall, the filter receiver 60 and the support webs 92 form a carrier support for supporting the long-term filter 62.

The filter holder 58, the long-term filter 62 and the holding ring 66 are fixedly connected to one another, for example by welding or adhesive bonding. In the assembled state, the coil springs 88 press the filter cartridge 54 onto the underside 36 of the lid, with the filter cartridge 54 being sealed against the underside 36 of the lid by means of the sealing ring 70.

The holding ring 66 has an outer ring and an inner ring 94 running concentrically therewith, from which four holding ring webs 96 disposed radially and symmetrically stabilize the holding ring 66.

On account of the offset arrangement of support web 92 and protective web 88, the long-term filter 62 supported on the support webs 92 is protected from direct mechanical damage. However, the long-term filter 62 is virtually unprotected on its side facing toward the opening 26. For this purpose, a protective cover 98, which is of mirror-symmetrical configuration and has a cover surface 100 curved convexly away from the top side 37 of the cover, is provided as a protective element; when the cover surface 100 is seen in plan view, it is in the shape of a non-equilateral octagon with short sides 102 and long sides 104.

An annular strip 108, which comprises four cutouts 110, each disposed diametrically in pairs, protrudes from an underside 106 of the protective cover. These cutouts 110 are shaped in such a manner that they can engage over the webs 30 and the protective cover 98 rests on the webs 30. Two spacer strips 112, which cross one another, are disposed on the underside 106 of the protective cover, as additional spacers, which spacer strips, in the region of the cutouts 110, project outward beyond the ring strip 108 as far as the long sides 104. When the protective cover 98 has been fitted, these strips rest on the annular surface 34.

To secure the protective cover 98 there are four latching connectors 114, which each comprise three limbs, which are disposed at right angles to one another, form a U-shaped frame 116 and two of which protrude radially outward from the ring strip 108. As free ends of the spacer strips 112, they form spacers resting on the annular surface 34. From a transverse web 118 of the frame 116, two latching arms 120 protrude parallel and at right angles from the underside 106 of the protective cover, which latching arms are provided at their free ends with a latching lug 122 protruding at right angles. The four latching connectors 114 are disposed in diametrically opposite pairs on the protective cover 98.

To secure the protective cover 98, the latter is moved perpendicularly toward the top side 37 of the lid and is oriented in such a way that the cutouts 110 each face toward a web 30 and the latching arms 120 each slide into one of the two indentations 32 and 33. As soon as the cutouts 110 rest on the webs 30, the closure strips 112 and the frames 116 rest on the annular surface 34, the latching arms 120 latch to the opening rim 28 as a result of the latching lugs 122 engaging behind the opening rim 28.

The size of the protective cover 98 is selected to be such that in the inserted position the annular surface 34 is completely covered. The short sides 102 then rest on the support surfaces 42, while the long sides 104 run parallel to the side edges of the lid 14 and in each case partially cover the inflow edges 40. When the protective cover 98 is inserted, the long-term filter 62 held in the filter cartridge 54 is also completely protected from mechanical damage from its other side.

Figure 2:
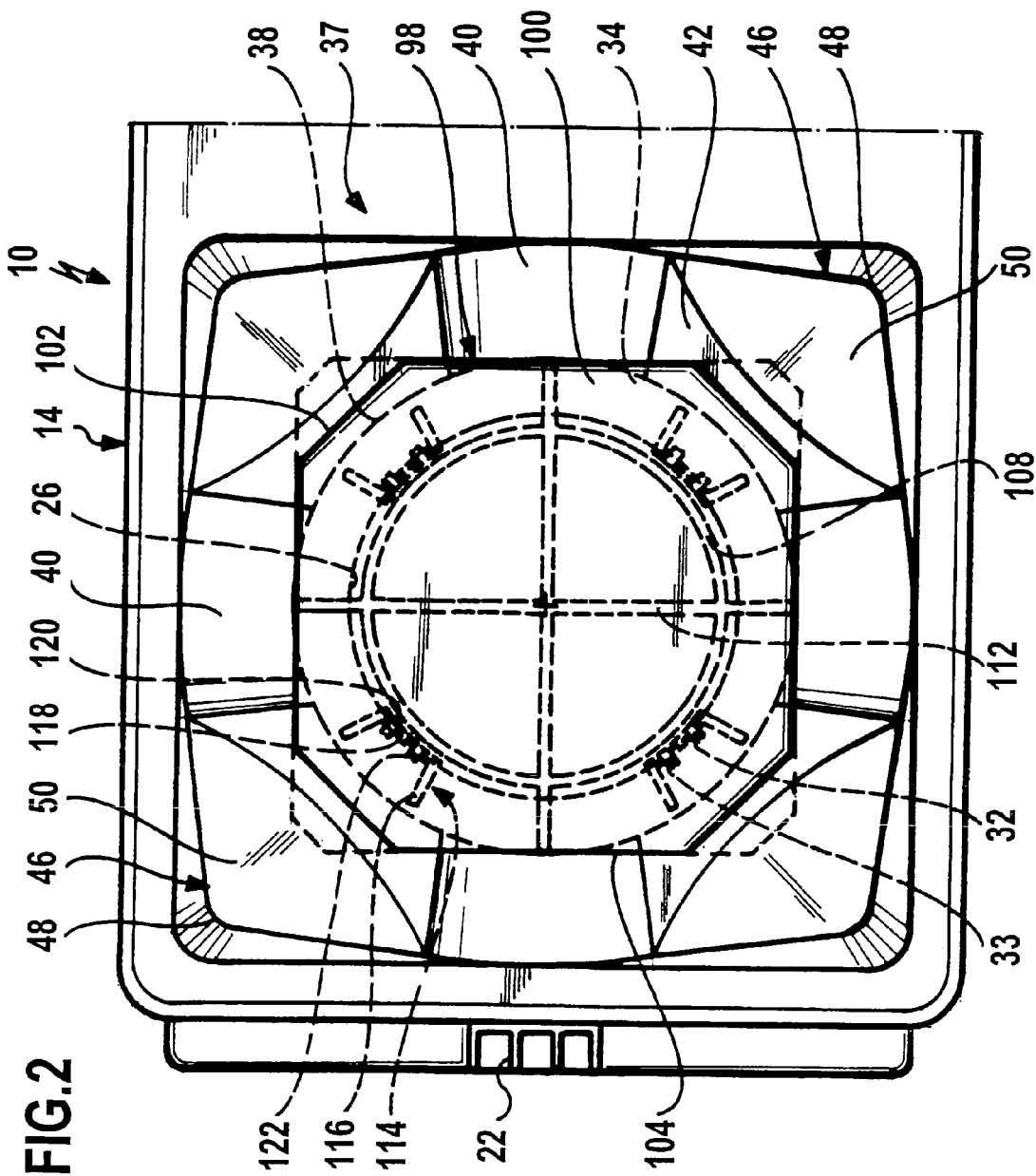
FIG. 2 shows a plan view of an excerpt of a sterile container.
Figure 3:
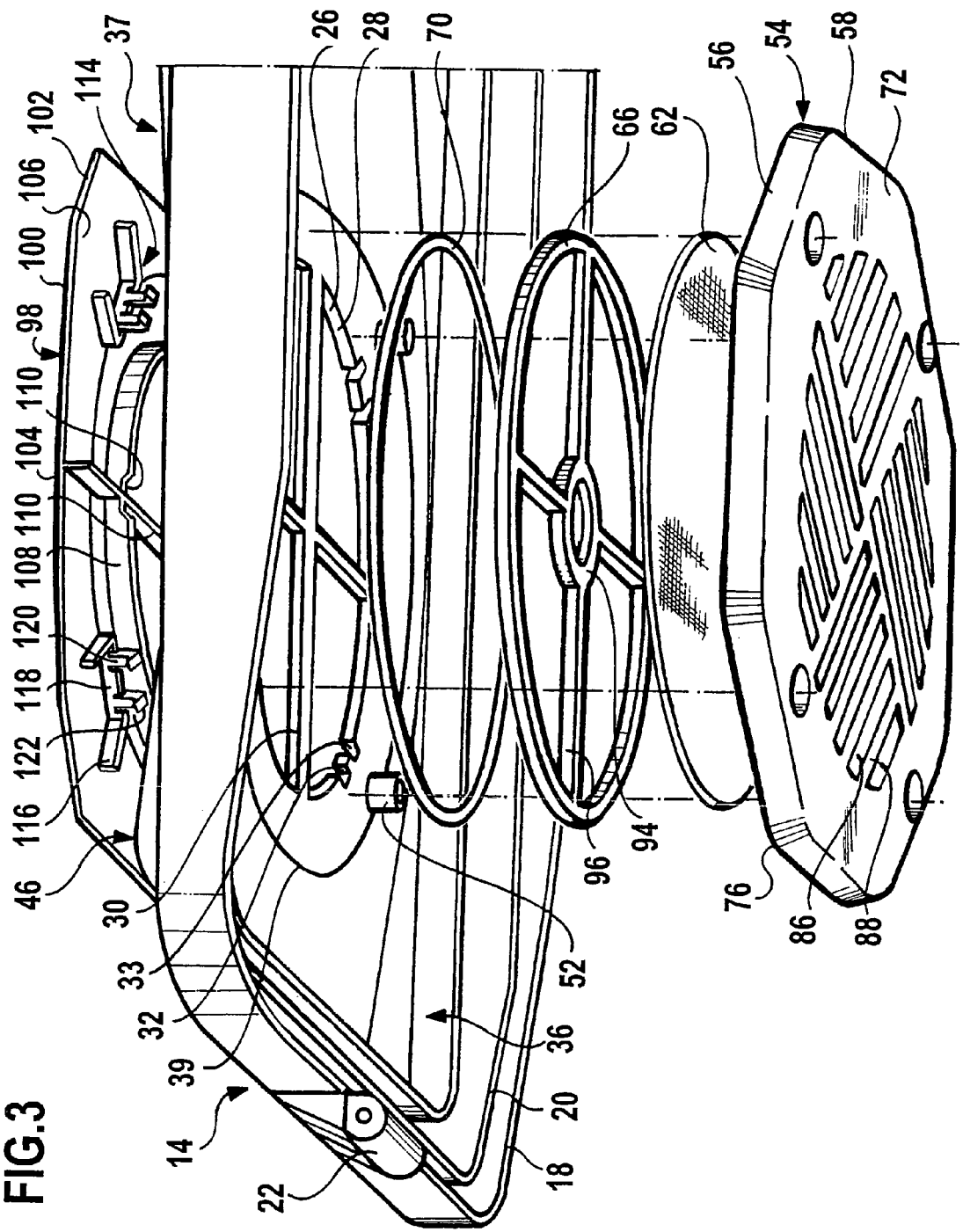
FIG. 3 shows an exploded view of an excerpt of a lid of the sterile container.
Figure 4:
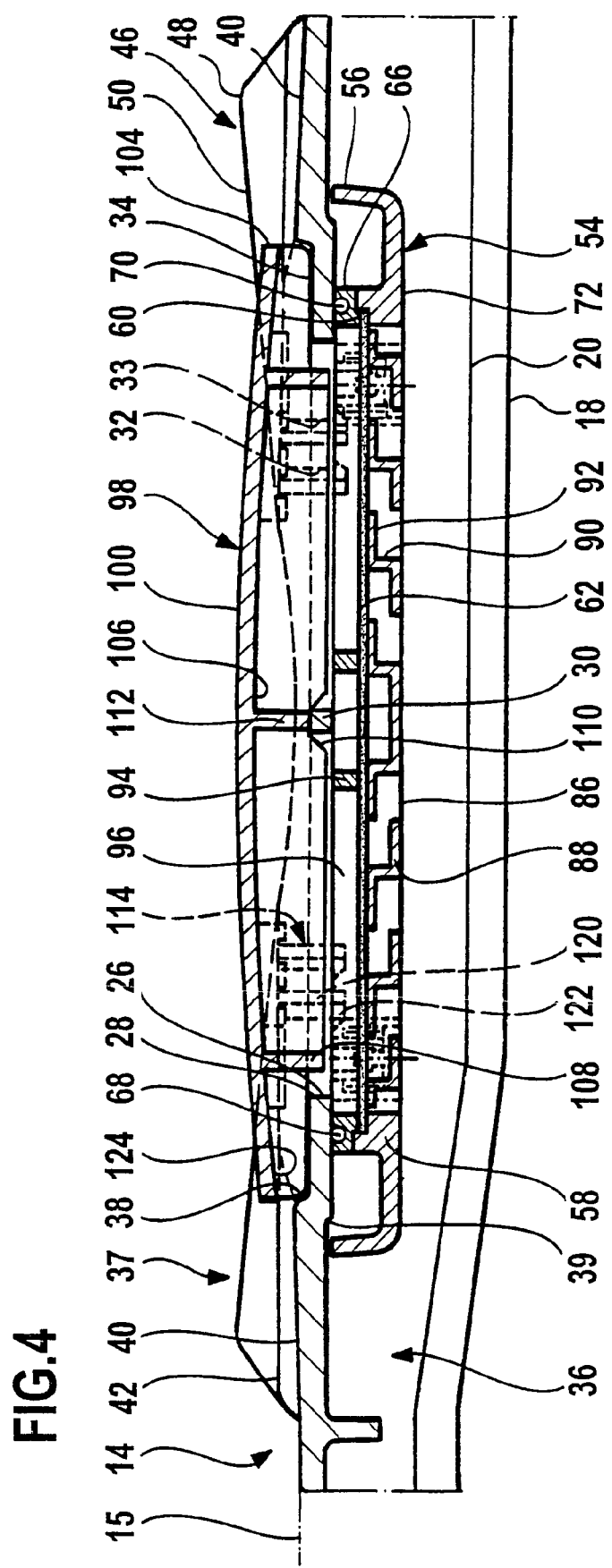
FIG. 4 shows a partially cut-away cross-sectional view through an excerpt of a lid.
Figure 5:
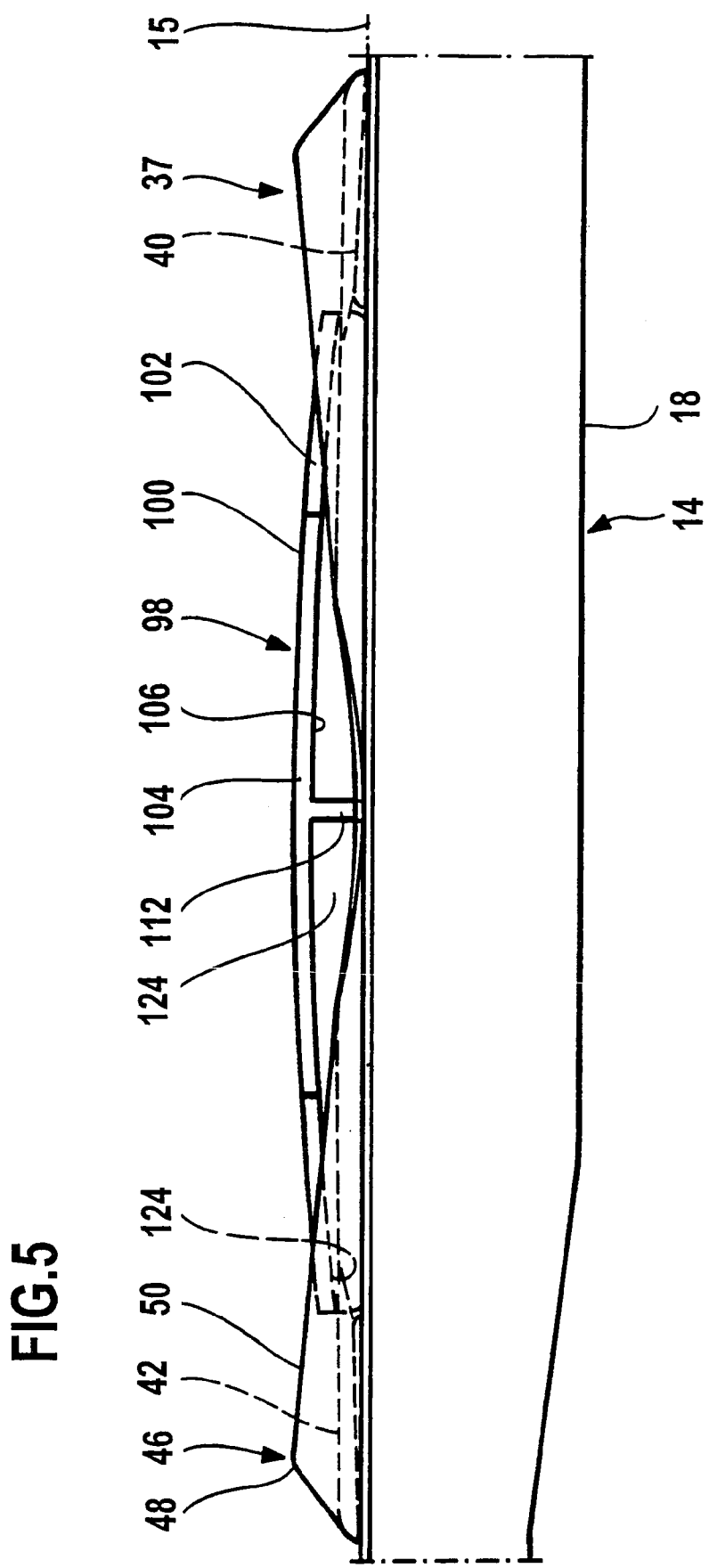
FIG. 5 shows a partially cut-away side view of an excerpt of a lid.
Figure 6:
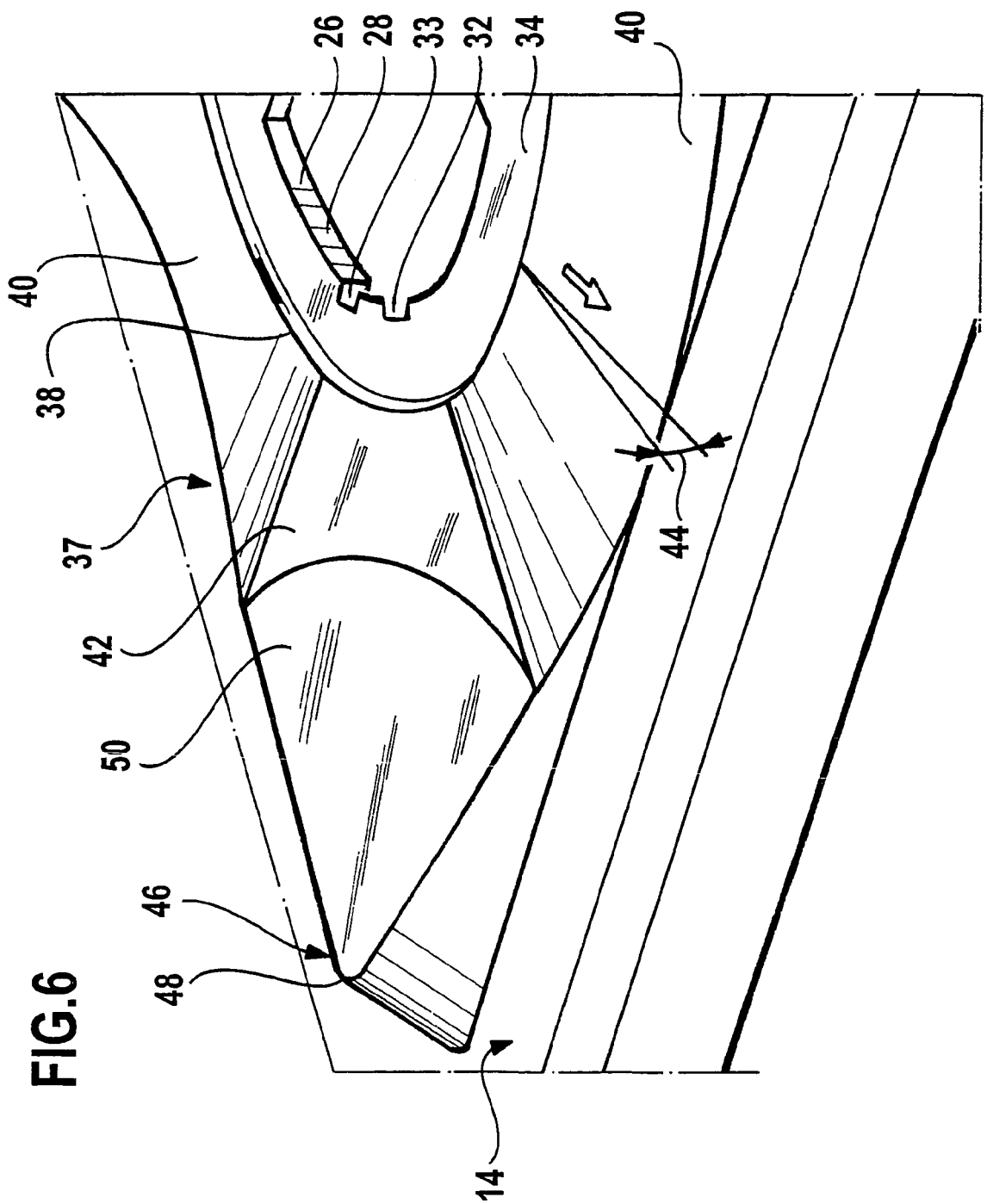
FIG. 6 shows an enlarged, perspective partial view of a lid.
Figure 7:
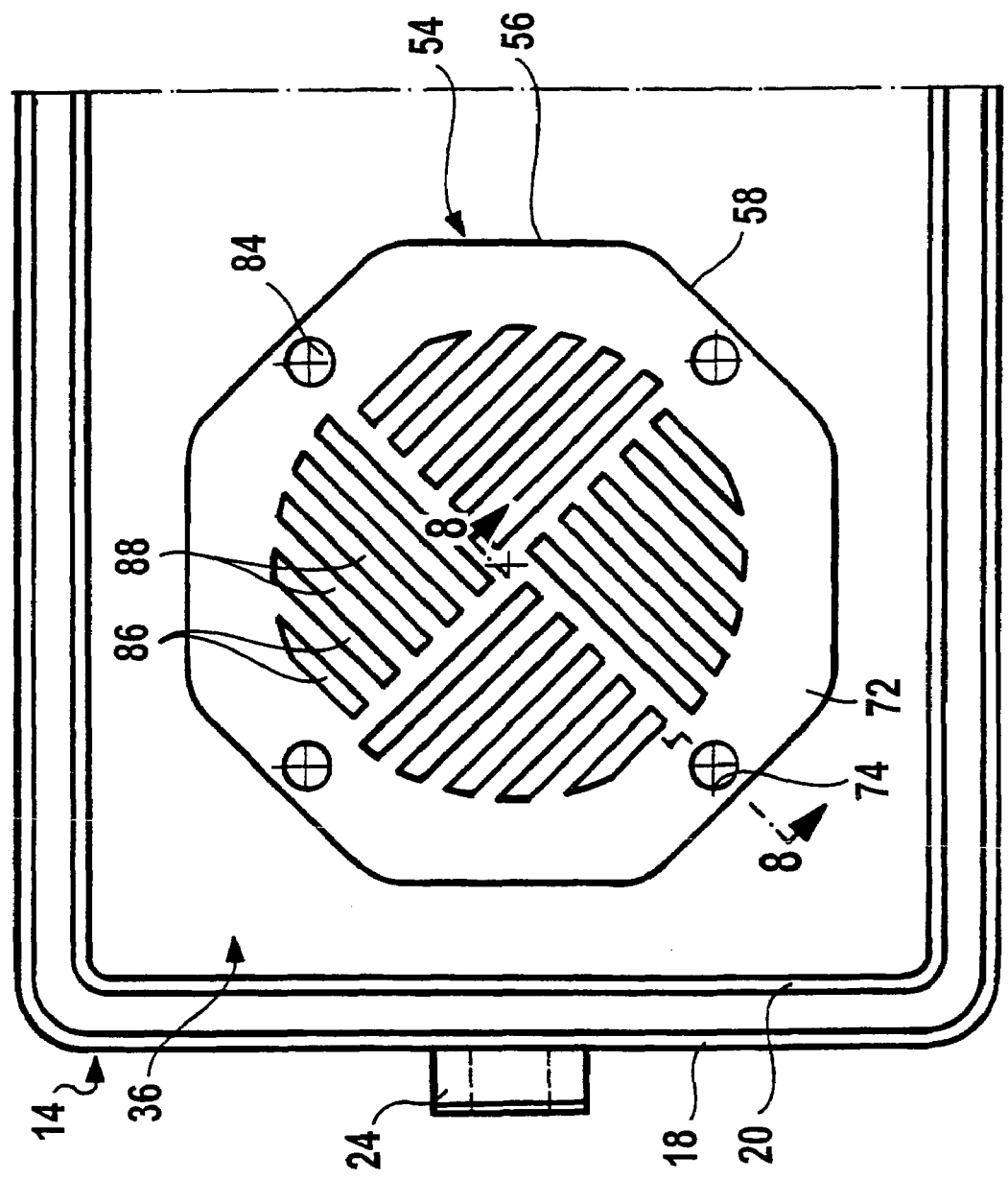
FIG. 7 shows a view onto the underside of half of a lid.

In an alternative variant of a lid, which is indicated by dot-dashed lines in FIG. 2, the long sides 104 of the protective cover 98 are lengthened. The pyramid 46 then has, in its run-off surface 50, an additional recess, in which the short side 102 of the protective cover 98 is fitted. This results in a seamless transition between the run-off surface 50 and the cover surface 100.

The highest point of the protective cover 98 when the latter is inserted lies beneath the highest point of the four pyramids 46, so that when sterile containers 10 are stacked on top of one another the container 12 which is mounted on the lid 14 rests only on the apexes 48 of the pyramids 46 but does not touch the protective covers 98.

If, with a substantially horizontally mounted sterile container 10, liquid reaches the top side 37 of the lid, for example reaches the protective cover 98, the curvature of the protective cover 98 means that the liquid can flow off to the short or long sides 102 or 104, respectively. From the long sides 104, the liquid passes onto the inflow edges 40, from which the liquid can flow off to the sides of the lid 14 on account of the inclination of these edges.

When the protective cover 98 is fitted, a substantially double-convex lens-shaped inflow opening 124, as seen in side view, is formed, through which a gaseous fluid can flow in and out. The fluid then flows substantially parallel to the lid plane 15, through the opening 26 substantially perpendicular thereto. In a basic position illustrated in FIG. 8, the filter cartridge 54 engages against the underside 36 of the lid, sealed off by means of the sealing ring 70. If the sterile container 10 is exposed to hot steam, the latter flows to the long-term filter 62, as described above. It passes through the long-term filter 62 and then follows a flow channel, defined by the support web 92, the strip 90 and the protective web 88, into the interior of the container 12.

Figure 8:
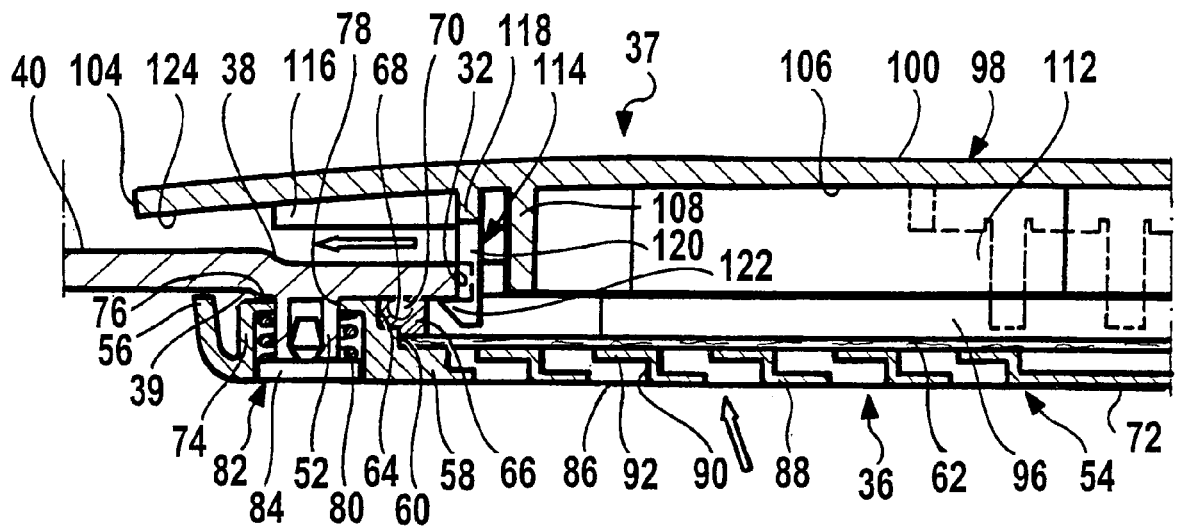
FIG. 8 shows a cross-sectional view of an excerpt of a filter cartridge which is mounted in a gastight manner on the lid.
Figure 9:
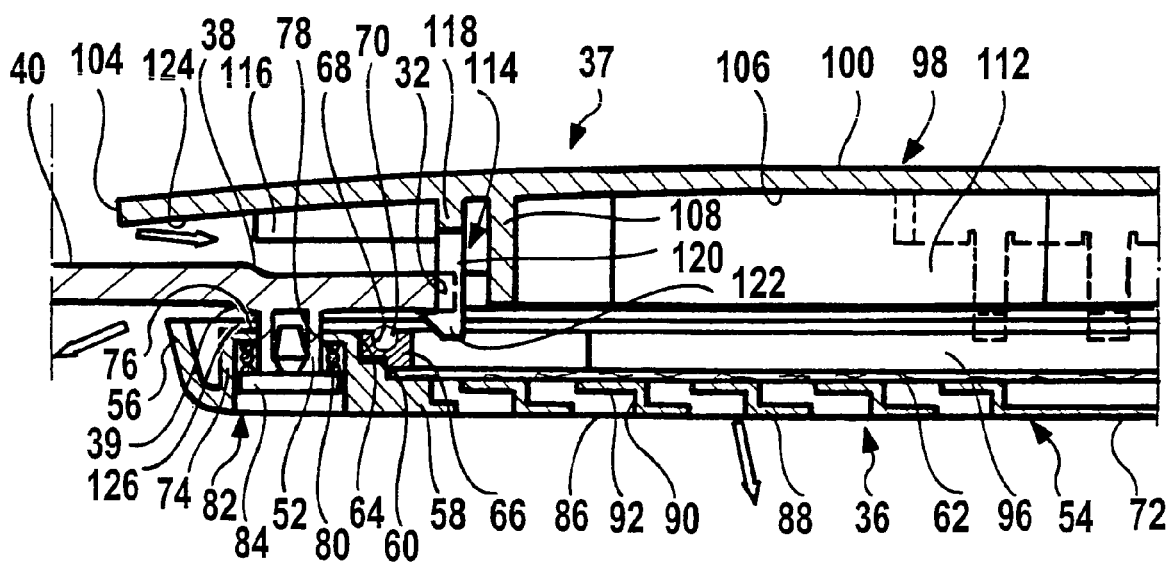
FIG. 9 shows a cross-sectional view of an excerpt similar to that shown in FIG. 8, with a filter cartridge lifted off.

If a pressure acting from outside on the sterile container 10 exceeds a force which can be set by means of the coil springs 80, the filter cartridge 54, which is mounted resiliently on the lid 14, acts as a pressure-relief valve. The filter cartridge 54 is lifted off the underside 36 of the lid and opens up a flow channel 126 which is closed in the basic position, as illustrated in FIG. 9. Hot steam can now pass not only through the long-term filter 62 but also into the interior of the container 12 via the flow channel 126. As soon as the pressure gradient drops again, the coil springs 80 press the filter cartridge 54 back onto the underside of the lid, so that steam or gas can only flow in and out via the long-term filter 62. FIGS. 8 and 9 use arrows to indicate the incoming and outgoing flow of a gas or steam.

Figure 10:
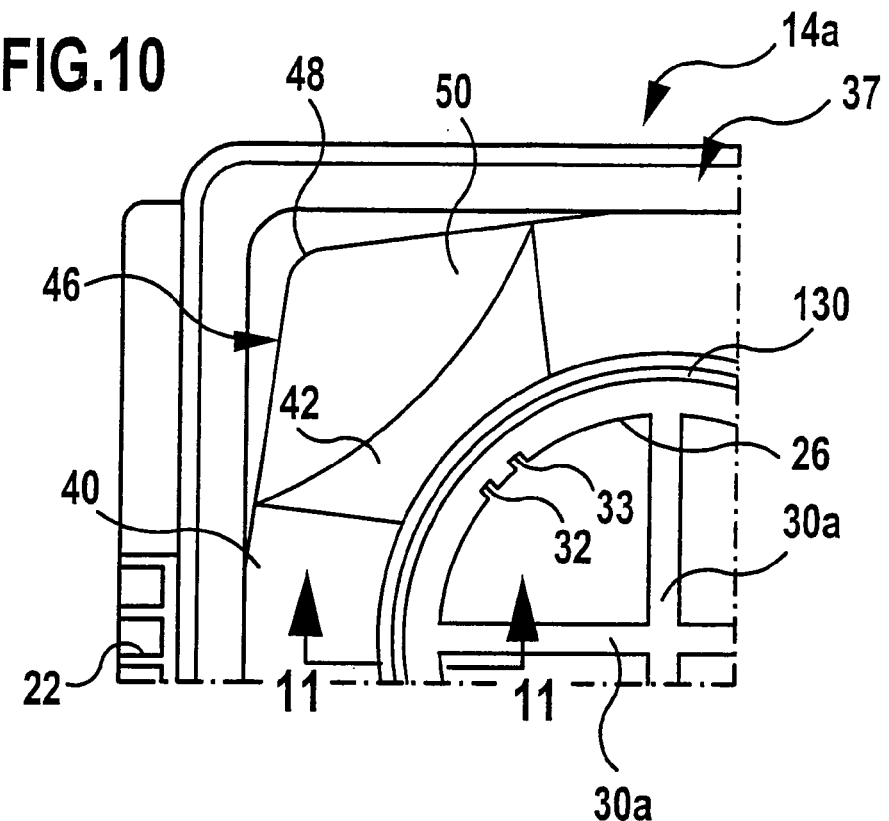
FIG. 10 shows a plan view of an excerpt of an alternative configuration of a lid.
Figure 11:
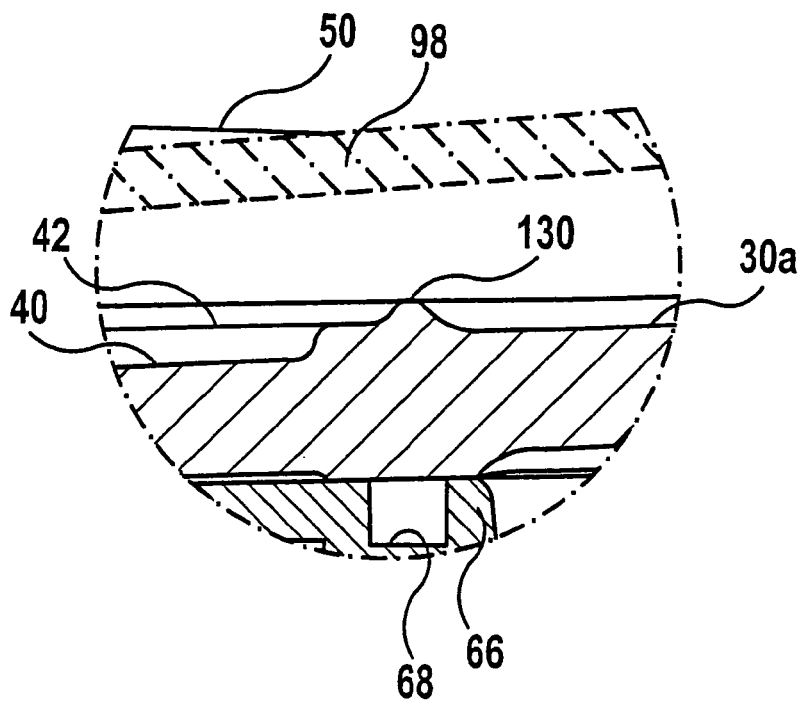
FIG. 11 shows a cross-sectional view 11—11 of an excerpt from FIG. 10.

A slightly modified variant of the lid 14a will now be explained in more detail with reference to FIGS. 10 and 11.

In a lid 14 as has been explained in connection with FIGS. 1 to 9, it is possible to provide, as an additional element, a fluid-retaining element in the form of an encircling edge 130. The encircling edge 130 is formed as an annular projection which protrudes from the top side 37 of the lid and surrounds the opening 26 on the top side 37 of the lid. In the exemplary embodiment illustrated, the edge adjoins the annular edge 38 on the outer side toward the inflow edge 40, with a short spacing between them. Alternatively, however, it would also be conceivable for the edge 130 to directly adjoin the opening rim 28 or the annular edge 38. If the gas exchange openings in the lid 14 are not circular in form, it is preferable for the edge 130 to follow the contour of the opening. The long side 104 of the protective cover 98 projects beyond the edge 130, so that liquid which runs off the protective cover 98 drops directly onto the inflow edge 40 but cannot pass over the edge 130, which forms a barrier, through the opening 26 and onto the long-term filter 62. Furthermore, the webs 30a are offset away from the opening 26 and the top side 37 of the lid, so that, unlike in the case of the lid 14 described in connection with FIGS. 1 to 9, a set-back annular surface 34 is not formed.

The container 12 may optionally be made from metal or plastic. The lid 14 is preferably made completely from a plastic, for example from polyether ether ketone or polyphenylene sulfone. The long-term filter is preferably made from polytetrafluorethylene.

The invention claimed is:

1. Sterile container, comprising:
a holding space,
a lid for closing the holding space,
a gas exchange opening in said lid, and
a protective element,
said holding space being defined by a container base and container walls,
said gas exchange opening adapted to be closed off by a sterile filter, said protective element covering the sterile filter at a spacing therefrom, said protective element being disposed on an outer side of the lid and being non-perforated in an area sufficient to completely cover the gas exchange opening,
wherein on the outer side of the lid there is provided at least one inflow edge which faces away from the gas exchange opening and slopes downward toward the outside relative to a lid plane.

2. Sterile container comprising:
a holding space, said holding space being defined by a container base and container walls;
a lid for closing the holding space;
a gas exchange opening in said lid, said gas exchange opening adapted to be closed off by a sterile filter; and
a protective element, said protective element covering the sterile filter at a spacing therefrom, wherein:
on an outer side of the lid there is provided at least one inflow edge which faces away from the gas exchange opening and slopes downward toward the outside relative to a lid plane;
there is provided, between the protective element and the lid, at least one opening for the passage of gas, which is in fluid communication with the gas exchange opening; and
the opening for the passage of gas, in cross section, has a double-convex lens shape.

3. Sterile container according to claim 1, wherein an angle of inclination which is included by the inflow edge and the lid plane is at least 1 degree.

4. Sterile container according to claim 2, wherein the protective element is disposed on the outer side of the lid.

5. Sterile container according to claim 1, wherein the lid, on its outer side, has a seating surface for seating the protective element, which surrounds the gas exchange opening.

6. Sterile container according to claim 5, wherein the seating surface comprises an annular surface which runs parallel to the lid plane and is set back in the direction of the holding space.

7. Sterile container according to claim 5, wherein the protective element completely covers the gas exchange opening and the seating surface.

8. Sterile container according to claim 1, wherein there are provided support surfaces for the purpose of supporting the protective element connected to the lid.

9. Sterile container according to claim 1, wherein the protective element comprises spacing elements for maintaining a spacing between the protective element and the lid.

10. Sterile container according to claim 1, wherein the protective element comprises a reinforcing frame.

11. Sterile container according to claim 10, wherein the reinforcing frame comprises webs which cross one another and run substantially parallel to the lid plane.

12. Sterile container according to claim 11, wherein the spacing elements are formed by projections and/or at least in part by the webs.

13. Sterile container according to claim 1, wherein there is provided at least one snap-action connection for connecting the protective element to the lid.

14. Sterile container according to claim 13, wherein the at least one snap-action connection is provided for connection of the protective element to a rim, which includes latching recesses, of the gas exchange opening.

15. Sterile container according to claim 13, wherein the at least one snap-action connection comprises elastic spring arms which project away from the protective element toward the lid and are provided with a latching projection.

16. Sterile container according to claim 1, wherein there is provided, between the protective element and the lid, at least one opening for the passage of gas, which is in fluid communication with the gas exchange opening.

17. Sterile container according to claim 16, wherein the opening for the passage of gas is arranged in such a way that it becomes possible for gas to flow in a direction of flow running substantially transversely with respect to the flow-permitting direction through the sterile filter.

18. Sterile container according to claim 1, wherein the lid has at least one spacer element for stacking a further sterile container on the sterile container, so that gas exchange through the gas exchange opening is possible with stacked sterile containers.

19. Sterile container according to claim 2, wherein the lid has at least one spacer element for stacking a further sterile container on the sterile container, so that gas exchange through the gas exchange opening is possible with stacked sterile containers.

20. Sterile container according to claim 18, wherein the inflow edge is disposed between two spacer elements.

21. Sterile container according to claim 18, wherein the spacer elements comprise at least three projections facing away from the outer side of the sterile container.

22. Sterile container according to claim 18, wherein:
the lid, on its outer side, has a seating surface for seating the protective element, which surrounds the gas exchange opening; and
the seating surface is delimited by the at least one inflow edge and the at least one spacer element.

23. Sterile container according to claim 18, wherein
there are provided support surfaces for the purpose of supporting the protective element connected to the lid; and
the at least one spacer elements comprises or adjoins the support surfaces.

24. Sterile container according to claim 18, wherein the lid, the at least one spacer element, the seating surface and the at least one inflow edge are formed integrally.

25. Sterile container according to claim 1, wherein there is provided a filter unit, which comprises the sterile filter, a carrier and a holding element, and wherein the sterile filter is held between the carrier and the holding element.

26. Sterile container according to claim 2, wherein there is provided a filter unit, which comprises the sterile filter, a carrier and a holding element, and wherein the sterile filter is held between the carrier and the holding element.

27. Sterile container according to claim 18, wherein there is provided a filter unit, which comprises the sterile filter, a carrier and a holding element, and wherein the sterile filter is held between the carrier and the holding element.

28. Sterile container according to claim 25, wherein the filter unit is in single-piece form, and wherein the carrier, the sterile filter and the holding element are nonreleasably connected to one another.

29. Sterile container according to claim 25, wherein the filter unit is mounted moveably, wherein the filter unit, in a closed position, closes a flow path and, in a flow-permitting position, opens the flow path, so that gas exchange in the closed position is possible only through the sterile filter and in the flow-permitting position is possible through the sterile filter and/or through the flow path.

30. Sterile container according to claim 25, wherein there is provided a pressure-relief valve, wherein the pressure-relief valve is disposed in such a way that in a basic position it adopts a closed position, that it adopts a flow-permitting position when a pressure in the vicinity of the sterile container exceeds a pressure in the sterile container by a predetermined pressure difference, and wherein the pressure-relief valve comprises the filter unit.

31. Sterile container according to claim 1, wherein the gas exchange opening comprises at least one reinforcing element for reinforcing the lid.

32. Sterile container according to claim 31, wherein the at least one reinforcing element is formed by a web which spans the gas exchange opening.

33. Sterile container according to claim 31, wherein the at least one reinforcing element is offset in a direction away from the holding space relative to the outer side of the lid.

34. Sterile container according to claim 1, wherein there is provided a fluid-retaining element for preventing fluid from flowing in from the outer side of the lid through the gas exchange opening.

35. Sterile container according to claim 2, wherein there is provided a fluid-retaining element for preventing fluid from flowing in from the outer side of the lid through the gas exchange opening.

36. Sterile container according to claim 25, wherein there is provided a fluid-retaining element for preventing fluid from flowing in from the outer side of the lid through the gas exchange opening.

37. Sterile container according to claim 34, wherein the fluid-retaining element is disposed on the outer side of the lid and surrounds the gas exchange opening at least in sections.

38. Sterile container according to claim 34, wherein the fluid-retaining element is formed as a rim which protrudes from the outer side of the lid.

39. Sterile container according to claim 34, wherein the fluid-retaining element is disposed at a spacing from the gas exchange opening.

40. Sterile container according to claim 34, wherein the protective element completely covers the gas exchange opening and the fluid-retaining element.

41. Sterile container according to claim 1, wherein the lid is made from a plastic.

42. Sterile container according to claim 34, wherein the lid is made from a plastic.

43. Sterile container according to claim 41, wherein the lid is made from polyether ether ketone (PEEK) or polyphenylene sulfone (PPSU).

44. Sterile container according to claim 42, wherein the lid is made from polyether ether ketone (PEEK) or polyphenylene sulfone (PPSU).

45. Sterile container according to claim 1, wherein the protective element is releasably connected to the lid.

* * * * *

UNITED STATES PATENT AND TRADEMARK OFFICE
CERTIFICATE OF CORRECTION

PATENT NO. : 7,172,740 B2  
APPLICATION NO. : 10/845780  
DATED : February 6, 2007  
INVENTOR(S) : Gleichauf et al.

Page 1 of 1

It is certified that error appears in the above-identified patent and that said Letters Patent is hereby corrected as shown below:

On the Title of the patent, the Assignee is corrected to read:

Insert Item  
    (73) Assignee: AESCULAP AG & Co. KG, Tuttlingen (DE)

Signed and Sealed this

Ninth Day of October, 2007

JON W. DUDAS  
*Director of the United States Patent and Trademark Office*